US008053231B2

(12) United States Patent
Nishihira et al.

(10) Patent No.: US 8,053,231 B2
(45) Date of Patent: Nov. 8, 2011

(54) DNA VACCINE

(75) Inventors: Jun Nishihira, Sapporo (JP); Yoshikazu Koyama, Sapporo (JP); Shin Onodera, Sapporo (JP)

(73) Assignee: Jun Nishihira, Hokkaido (JP)

(*) Notice: Subject to any disclaimer, the term of this patent is extended or adjusted under 35 U.S.C. 154(b) by 801 days.

(21) Appl. No.: 11/730,745

(22) Filed: Apr. 3, 2007

(65) Prior Publication Data

US 2008/0247994 A1 Oct. 9, 2008

(51) Int. Cl.
*C12N 15/63* (2006.01)
*C12N 15/62* (2006.01)
*C12N 15/79* (2006.01)
*A61K 48/00* (2006.01)
*C07H 21/04* (2006.01)

(52) U.S. Cl. .................. 435/320.1; 514/44 R; 536/23.4

(58) Field of Classification Search ........................ None
See application file for complete search history.

(56) References Cited

U.S. PATENT DOCUMENTS 5,986,060 A * 11/1999 Li et al. ......................... 530/351
2002/0090379 A1 7/2002 Mouritsen et al.

FOREIGN PATENT DOCUMENTS

WO    WO 95/05849 A1    3/1995

OTHER PUBLICATIONS

Onodera, S. et al., "A novel DNA vaccine targeting macrophage migration inhibitory factor protects joint inflammation and destruction in murine models of arthritis", Feb. 2007, Arthritis and Rheum., vol. 56: pp. 521-530.*
Dalum et al., "Therapeutic antibodies elicited by immunization against TNF-α," Nature Biotechnology, Jul. 1999, 17:666-669.
Hertz et al., "Active Vaccination Against IL-5 Bypasses Immunological Tolerance and Ameliorates Experimental Asthma," The Journal of Immunology, 2001, 167:3792-3799.
Wildbaum et al., "Beneficial Autoimmunity to Proinflammatory Mediators Restrains the Consequences of Self-Destructive Immunity," Immunity, Nov. 2003, 19:679-688.
American Journal of Tropical Medicine and Hygiene, 2000, 62(3,Supp):193-194, Meeting info.: 49th Annual Meeting of the American Society of Tropical Medicine and Hygiene, Houston, Texas, Oct. 29-Nov. 2, 2000.
Zang et al., "Homologues of Human Macrophage Migration Inhibitory Factor from a Parasitic Nematode," J. Biol. Chem., Nov. 15, 2002, 277(46):44261-44267.

* cited by examiner

*Primary Examiner* — Michael Burkhart
(74) *Attorney, Agent, or Firm* — Foley & Lardner LLP

(57) ABSTRACT

The present invention relates to a DNA vaccine consisting of a vector expressing a part or the whole of a polypeptide regulating production of an inflammatory cytokine, a pharmaceutical composition comprising the DNA vaccine, and a method of preventing or treating an inflammatory disease by using the pharmaceutical composition.

5 Claims, 3 Drawing Sheets

FIG. 1

SEQUENCE LISTING

```
<160> NUMBER OF SEQ ID NOS: 42

<210> SEQ ID NO 1
<211> LENGTH: 115
<212> TYPE: PRT
<213> ORGANISM: Homo sapiens

<400> SEQUENCE: 1

Met Pro Met Phe Ile Val Asn Thr Asn Val Pro Arg Ala Ser Val Pro
1               5                   10                  15

Asp Gly Phe Leu Ser Glu Leu Thr Gln Gln Leu Ala Gln Ala Thr Gly
            20                  25                  30

Lys Pro Pro Gln Tyr Ile Ala Val His Val Val Pro Asp Gln Leu Met
        35                  40                  45
```

```
Ala Phe Gly Gly Ser Ser Glu Pro Cys Ala Leu Cys Ser Leu His Ser
        50                  55                  60

Ile Gly Lys Ile Gly Gly Ala Gln Asn Arg Ser Tyr Ser Lys Leu Leu
 65                  70                  75                  80

Cys Gly Leu Leu Ala Glu Arg Leu Arg Ile Ser Pro Asp Arg Val Tyr
                 85                  90                  95

Ile Asn Tyr Tyr Asp Met Asn Ala Ala Asn Val Gly Trp Asn Asn Ser
                100                 105                 110

Thr Phe Ala
        115

<210> SEQ ID NO 2
<211> LENGTH: 115
<212> TYPE: PRT
<213> ORGANISM: Rattus norvegicus

<400> SEQUENCE: 2

Met Pro Met Phe Ile Val Asn Thr Asn Val Pro Arg Ala Ser Val Pro
 1               5                  10                  15

Glu Gly Phe Leu Ser Glu Leu Thr Gln Gln Leu Ala Gln Ala Thr Gly
                 20                  25                  30

Lys Pro Ala Gln Tyr Ile Ala Val His Val Val Pro Asp Gln Leu Met
                 35                  40                  45

Thr Phe Ser Gly Thr Ser Asp Pro Cys Ala Leu Cys Ser Leu His Ser
        50                  55                  60

Ile Gly Lys Ile Gly Gly Ala Gln Asn Arg Asn Tyr Ser Lys Leu Leu
 65                  70                  75                  80

Cys Gly Leu Leu Ser Asp Arg Leu His Ile Ser Pro Asp Arg Val Tyr
                 85                  90                  95

Ile Asn Tyr Tyr Asp Met Asn Ala Ala Asn Val Gly Trp Asn Gly Ser
                100                 105                 110

Thr Phe Ala
        115

<210> SEQ ID NO 3
<211> LENGTH: 115
<212> TYPE: PRT
<213> ORGANISM: Mus musculus

<400> SEQUENCE: 3

Met Pro Met Phe Ile Val Asn Thr Asn Val Pro Arg Ala Ser Val Pro
 1               5                  10                  15

Glu Gly Phe Leu Ser Glu Leu Thr Gln Gln Leu Ala Gln Ala Thr Gly
                 20                  25                  30

Lys Pro Ala Gln Tyr Ile Ala Val His Val Val Pro Asp Gln Leu Met
                 35                  40                  45

Thr Phe Ser Gly Thr Asn Asp Pro Cys Ala Leu Cys Ser Leu His Ser
        50                  55                  60

Ile Gly Lys Ile Gly Gly Ala Gln Asn Arg Asn Tyr Ser Lys Leu Leu
 65                  70                  75                  80

Cys Gly Leu Leu Ser Asp Arg Leu His Ile Ser Pro Asp Arg Val Tyr
                 85                  90                  95

Ile Asn Tyr Tyr Asp Met Asn Ala Ala Asn Val Gly Trp Asn Gly Ser
                100                 105                 110

Thr Phe Ala
        115
```

```
<210> SEQ ID NO 4
<211> LENGTH: 21
<212> TYPE: PRT
<213> ORGANISM: Artificial
<220> FEATURE:
<223> OTHER INFORMATION: Tetanus toxin P30

<400> SEQUENCE: 4

Phe Asn Asn Phe Thr Val Ser Phe Trp Leu Arg Val Pro Lys Val Ser
1               5                   10                  15

Ala Ser His Leu Glu
            20

<210> SEQ ID NO 5
<211> LENGTH: 71
<212> TYPE: DNA
<213> ORGANISM: Artificial
<220> FEATURE:
<223> OTHER INFORMATION: Nucleotide sequence encoding Tetanus toxin P30

<400> SEQUENCE: 5
ggaattcaac aacttcaccg tgagcttctg gctgcgcgtg cccaaggtga gcgccagcca      60
cctggaattc c                                                         71

<210> SEQ ID NO 6
<211> LENGTH: 35
<212> TYPE: DNA
<213> ORGANISM: Artificial
<220> FEATURE:
<223> OTHER INFORMATION: Primer B-1U

<400> SEQUENCE: 6
cgggatccgc caccatgcct atgttcatcg tgaac                                35

<210> SEQ ID NO 7
<211> LENGTH: 25
<212> TYPE: DNA
<213> ORGANISM: Artificial
<220> FEATURE:
<223> OTHER INFORMATION: Primer E-93L

<400> SEQUENCE: 7
ggaattcggt ggcctgcgcc agctg                                           25

<210> SEQ ID NO 8
<211> LENGTH: 25
<212> TYPE: DNA
<213> ORGANISM: Artificial
<220> FEATURE:
<223> OTHER INFORMATION: Promer E-112U

<400> SEQUENCE: 8
ggaattcatc gcagtgcacg tggtc                                           25

<210> SEQ ID NO 9
<211> LENGTH: 27
<212> TYPE: DNA
<213> ORGANISM: Artificial
<220> FEATURE:
<223> OTHER INFORMATION: Primer X-348L

<400> SEQUENCE: 9
ccgctcgagt taagcgaagg tggaacc                                         27

<210> SEQ ID NO 10
<211> LENGTH: 45
```

```
<212> TYPE: DNA
<213> ORGANISM: Artificial
<220> FEATURE:
<223> OTHER INFORMATION: Primer E-TxU

<400> SEQUENCE: 10
ggaattcaac aacttcaccg tgagcttctg gctgcgcgtg cccaa        45

<210> SEQ ID NO 11
<211> LENGTH: 45
<212> TYPE: DNA
<213> ORGANISM: Artificial
<220> FEATURE:
<223> OTHER INFORMATION: Primer E-TxL

<400> SEQUENCE: 11
ggaattccag gtggctggcg ctcaccttgg gcacgcgcag ccaga        45

<210> SEQ ID NO 12
<211> LENGTH: 81
<212> TYPE: PRT
<213> ORGANISM: Mus musculus

<400> SEQUENCE: 12

Met Ser Thr Glu Ser Met Ile Arg Asp Val Glu Leu Ala Glu Glu Ala
1               5                   10                  15

Leu Pro Gln Lys Met Gly Gly Phe Gln Asn Ser Arg Arg Cys Leu Cys
            20                  25                  30

Leu Ser Leu Phe Ser Phe Leu Leu Val Ala Gly Ala Thr Thr Leu Phe
        35                  40                  45

Cys Leu Leu Asn Phe Gly Val Ile Gly Pro Gln Arg Asp Glu Lys Phe
    50                  55                  60

Pro Asn Gly Leu Pro Leu Ile Ser Ser Met Ala Gln Thr Leu Thr Leu
65                  70                  75                  80

Arg

<210> SEQ ID NO 13
<211> LENGTH: 243
<212> TYPE: DNA
<213> ORGANISM: Mus musculus

<400> SEQUENCE: 13
atgagcacag aaagcatgat ccgcgacgtg aactggcag aagaggcact ccccaaaag      60 atggggggct tccagaactc caggcggtgc tatgtctca gcctcttctc attcctgctt     120
gtggcagggg ccaccacgct cttctgtcta ctgaacttcg gggtgatcgg tccccaaagg    180
gatgagaagt tcccaaatgg cctccctctc atcagttcta tggcccagac cctcacactc    240
aga                                                                  243

<210> SEQ ID NO 14
<211> LENGTH: 35
<212> TYPE: DNA
<213> ORGANISM: Artificial
<220> FEATURE:
<223> OTHER INFORMATION: Primer B-TsU

<400> SEQUENCE: 14
cgggatccgc caccatgagc acagaaagca tgatc        35

<210> SEQ ID NO 15
<211> LENGTH: 18
<212> TYPE: DNA
```

```
<213> ORGANISM: Artificial
<220> FEATURE:
<223> OTHER INFORMATION: Primer soe-TsL

<400> SEQUENCE: 15
tctgagtgtg agggtctg                                                    18

<210> SEQ ID NO 16
<211> LENGTH: 36
<212> TYPE: DNA
<213> ORGANISM: Artificial
<220> FEATURE:
<223> OTHER INFORMATION: Primer soe-Ts-MIFU

<400> SEQUENCE: 16
cagaccctca cactcagaat gcctatgttc atcgtg                                36

<210> SEQ ID NO 17
<211> LENGTH: 22
<212> TYPE: PRT
<213> ORGANISM: Mus musculus

<400> SEQUENCE: 17

Met Arg Arg Met Leu Leu His Leu Ser Val Leu Thr Leu Ser Cys Val
1               5                   10                  15

Trp Ala Thr Ala Met Glu
            20

<210> SEQ ID NO 18
<211> LENGTH: 66
<212> TYPE: DNA
<213> ORGANISM: Mus musculus

<400> SEQUENCE: 18
atgagaagga tgcttctgca cttgagtgtt ctgactctca gctgtgtctg ggccactgcc     60
atggag                                                                66

<210> SEQ ID NO 19
<211> LENGTH: 42
<212> TYPE: DNA
<213> ORGANISM: Artificial
<220> FEATURE:
<223> OTHER INFORMATION: Primer 5sU

<400> SEQUENCE: 19
atgagaagga tgcttctgca cttgagtgtt ctgactctca gc                        42

<210> SEQ ID NO 20
<211> LENGTH: 42
<212> TYPE: DNA
<213> ORGANISM: Artificial
<220> FEATURE:
<223> OTHER INFORMATION: Primer 5sL

<400> SEQUENCE: 20
ctccatggca gtggcccaga cacagctgag agtcagaaca ct                        42

<210> SEQ ID NO 21
<211> LENGTH: 33
<212> TYPE: DNA
<213> ORGANISM: Artificial
<220> FEATURE:
<223> OTHER INFORMATION: Primer B-5sU

<400> SEQUENCE: 21
```

-continued

```
cgggatccgc caccatgaga aggatgcttc tgc                                  33

<210> SEQ ID NO 22
<211> LENGTH: 30
<212> TYPE: DNA
<213> ORGANISM: Artificial
<220> FEATURE:
<223> OTHER INFORMATION: soe-5sL

<400> SEQUENCE: 22
acataggcat ctccatggca gtggcccaga                                      30

<210> SEQ ID NO 23
<211> LENGTH: 30
<212> TYPE: DNA
<213> ORGANISM: Artificial
<220> FEATURE:
<223> OTHER INFORMATION: Primer soe-5s-MIFU

<400> SEQUENCE: 23
tgccatggag atgcctatgt tcatcgtgaa                                      30

<210> SEQ ID NO 24
<211> LENGTH: 15
<212> TYPE: PRT
<213> ORGANISM: Gallus gallus

<400> SEQUENCE: 24

Ser Ala Leu Leu Ser Ser Asp Ile Thr Ala Ser Val Asn Cys Ala
1               5                   10                  15

<210> SEQ ID NO 25
<211> LENGTH: 45
<212> TYPE: DNA
<213> ORGANISM: Gallus gallus

<400> SEQUENCE: 25
agcgccctgc tgagcagcga catcaccgcc agcgtgaact gcgcc                     45

<210> SEQ ID NO 26
<211> LENGTH: 45
<212> TYPE: DNA
<213> ORGANISM: Artificial
<220> FEATURE:
<223> OTHER INFORMATION: Primer E-HLU

<400> SEQUENCE: 26
ggaattcagc gccctgctga gcagcgacat caccgccagc gtgaa                     45

<210> SEQ ID NO 27
<211> LENGTH: 30
<212> TYPE: DNA
<213> ORGANISM: Artificial
<220> FEATURE:
<223> OTHER INFORMATION: Primer E-HLL

<400> SEQUENCE: 27
ggaattcggc gcagttcacg ctggcggtga                                      30

<210> SEQ ID NO 28
<211> LENGTH: 12
<212> TYPE: PRT
<213> ORGANISM: Gallus gallus

<400> SEQUENCE: 28

Gln Ala Val His Ala Ala His Ala Glu Ile Asn Glu
```

```
<210> SEQ ID NO 29
<211> LENGTH: 36
<212> TYPE: DNA
<213> ORGANISM: Gallus gallus

<400> SEQUENCE: 29
caggccgtgc acgccgccca cgccgaaatc aacgaa                              36

<210> SEQ ID NO 30
<211> LENGTH: 30
<212> TYPE: DNA
<213> ORGANISM: Artificial
<220> FEATURE:
<223> OTHER INFORMATION: Primer E-OVU

<400> SEQUENCE: 30
ggaattccag gccgtgcacg ccgcccacgc                                     30

<210> SEQ ID NO 31
<211> LENGTH: 30
<212> TYPE: DNA
<213> ORGANISM: Artificial
<220> FEATURE:
<223> OTHER INFORMATION: Primer E-OVL

<400> SEQUENCE: 31
ggaattcgtt gatttcggcg tgggcggcgt                                     30

<210> SEQ ID NO 32
<211> LENGTH: 115
<212> TYPE: PRT
<213> ORGANISM: Artificial
<220> FEATURE:
<223> OTHER INFORMATION: DNA vaccine DV1

<400> SEQUENCE: 32
```

Met Pro Met Phe Ile Val Asn Thr Asn Val Pro Arg Ala Ser Val Pro
1               5                   10                  15

Glu Gly Phe Leu Ser Glu Leu Thr Gln Gln Leu Ala Gln Ala Thr Gly
            20                  25                  30

Lys Pro Ala Gln Tyr Ile Ala Val His Val Val Pro Asp Gln Leu Met
        35                  40                  45

Thr Phe Ser Gly Thr Ser Asp Pro Cys Ala Leu Cys Ser Leu His Ser
    50                  55                  60

Ile Gly Lys Ile Gly Gly Ala Gln Asn Arg Asn Tyr Ser Lys Leu Leu
65                  70                  75                  80

Cys Gly Leu Leu Ser Asp Arg Leu His Ile Ser Pro Arg Val Tyr
                85                  90                  95

Ile Asn Tyr Tyr Asp Met Asn Ala Ala Asn Val Gly Trp Asn Gly Ser
            100                 105                 110

Thr Phe Ala
        115

```
<210> SEQ ID NO 33
<211> LENGTH: 111
<212> TYPE: PRT
<213> ORGANISM: Artificial
<220> FEATURE:
<223> OTHER INFORMATION: DNA vaccine DV0

<400> SEQUENCE: 33
```

-continued

Met Pro Met Phe Ile Val Asn Thr Asn Val Pro Arg Ala Ser Val Pro
1               5                   10                  15

Glu Gly Phe Leu Ser Glu Leu Thr Gln Gln Leu Ala Gln Ala Thr Glu
            20                  25                  30

Phe Ile Ala Val His Val Pro Asp Gln Leu Met Thr Phe Ser Gly
        35                  40                  45

Thr Ser Asp Pro Cys Ala Leu Cys Ser Leu His Ser Ile Gly Lys Ile
    50                  55                  60

Gly Gly Ala Gln Asn Arg Asn Tyr Ser Lys Leu Leu Cys Gly Leu Leu
65                  70                  75                  80

Ser Asp Arg Leu His Ile Ser Pro Asp Arg Val Tyr Ile Asn Tyr Tyr
                85                  90                  95

Asp Met Asn Ala Ala Asn Val Gly Trp Asn Gly Ser Thr Phe Ala
            100                 105                 110

<210> SEQ ID NO 34
<211> LENGTH: 132
<212> TYPE: PRT
<213> ORGANISM: Artificial
<220> FEATURE:
<223> OTHER INFORMATION: DNA vaccine DV2

<400> SEQUENCE: 34

Met Pro Met Phe Ile Val Asn Thr Asn Val Pro Arg Ala Ser Val Pro
1               5                   10                  15

Glu Gly Phe Leu Ser Glu Leu Thr Gln Gln Leu Ala Gln Ala Thr Glu
            20                  25                  30

Phe Asn Asn Phe Thr Val Ser Phe Trp Leu Arg Val Pro Lys Val Ser
        35                  40                  45

Ala Ser His Leu Glu Phe Ile Ala Val His Val Pro Asp Gln Leu
    50                  55                  60

Met Thr Phe Ser Gly Thr Ser Asp Pro Cys Ala Leu Cys Ser Leu His
65                  70                  75                  80

Ser Ile Gly Lys Ile Gly Gly Ala Gln Asn Arg Asn Tyr Ser Lys Leu
                85                  90                  95

Leu Cys Gly Leu Leu Ser Asp Arg Leu His Ile Ser Pro Asp Arg Val
            100                 105                 110

Tyr Ile Asn Tyr Tyr Asp Met Asn Ala Ala Asn Val Gly Trp Asn Gly
        115                 120                 125

Ser Thr Phe Ala
    130

<210> SEQ ID NO 35
<211> LENGTH: 213
<212> TYPE: PRT
<213> ORGANISM: Artificial
<220> FEATURE:
<223> OTHER INFORMATION: DNA vaccine DV3

<400> SEQUENCE: 35

Met Ser Thr Glu Ser Met Ile Arg Asp Val Glu Leu Ala Glu Glu Ala
1               5                   10                  15

Leu Pro Gln Lys Met Gly Gly Phe Gln Asn Ser Arg Arg Cys Leu Cys
            20                  25                  30

Leu Ser Leu Phe Ser Phe Leu Leu Val Ala Gly Ala Thr Thr Leu Phe
        35                  40                  45

Cys Leu Leu Asn Phe Gly Val Ile Gly Pro Gln Arg Asp Glu Lys Phe
    50                  55                  60

Pro Asn Gly Leu Pro Leu Ile Ser Ser Met Ala Gln Thr Leu Thr Leu
65                  70                  75                  80

Arg Met Pro Met Phe Ile Val Asn Thr Asn Val Pro Arg Ala Ser Val
                85                  90                  95

Pro Glu Gly Phe Leu Ser Glu Leu Thr Gln Gln Leu Ala Gln Ala Thr
            100                 105                 110

Glu Phe Asn Asn Phe Thr Val Ser Phe Trp Leu Arg Val Pro Lys Val
        115                 120                 125

Ser Ala Ser His Leu Glu Phe Ile Ala Val His Val Val Pro Asp Gln
130                 135                 140

Leu Met Thr Phe Ser Gly Thr Ser Asp Pro Cys Ala Leu Cys Ser Leu
145                 150                 155                 160

His Ser Ile Gly Lys Ile Gly Gly Ala Gln Asn Arg Asn Tyr Ser Lys
                165                 170                 175

Leu Leu Cys Gly Leu Leu Ser Asp Arg Leu His Ile Ser Pro Asp Arg
            180                 185                 190

Val Tyr Ile Asn Tyr Tyr Asp Met Asn Ala Ala Asn Val Gly Trp Asn
        195                 200                 205

Gly Ser Thr Phe Ala
        210

<210> SEQ ID NO 36
<211> LENGTH: 154
<212> TYPE: PRT
<213> ORGANISM: Artificial
<220> FEATURE:
<223> OTHER INFORMATION: DNA vaccine DV4

<400> SEQUENCE: 36

Met Arg Arg Met Leu Leu His Leu Ser Val Leu Thr Leu Ser Cys Val
1               5                   10                  15

Trp Ala Thr Ala Met Glu Met Pro Met Phe Ile Val Asn Thr Asn Val
                20                  25                  30

Pro Arg Ala Ser Val Pro Glu Gly Phe Leu Ser Glu Leu Thr Gln Gln
            35                  40                  45

Leu Ala Gln Ala Thr Glu Phe Asn Asn Phe Thr Val Ser Phe Trp Leu
50                  55                  60

Arg Val Pro Lys Val Ser Ala Ser His Leu Glu Phe Ile Ala Val His
65                  70                  75                  80

Val Val Pro Asp Gln Leu Met Thr Phe Ser Gly Thr Ser Asp Pro Cys
                85                  90                  95

Ala Leu Cys Ser Leu His Ser Ile Gly Lys Ile Gly Gly Ala Gln Asn
            100                 105                 110

Arg Asn Tyr Ser Lys Leu Leu Cys Gly Leu Leu Ser Asp Arg Leu His
        115                 120                 125

Ile Ser Pro Asp Arg Val Tyr Ile Asn Tyr Tyr Asp Met Asn Ala Ala
130                 135                 140

Asn Val Gly Trp Asn Gly Ser Thr Phe Ala
145                 150

<210> SEQ ID NO 37
<211> LENGTH: 128
<212> TYPE: PRT
<213> ORGANISM: Artificial
<220> FEATURE:
<223> OTHER INFORMATION: DNA vaccine DV5

<400> SEQUENCE: 37

```
Met Pro Met Phe Ile Val Asn Thr Asn Val Pro Arg Ala Ser Val Pro
1               5                   10                  15

Glu Gly Phe Leu Ser Glu Leu Thr Gln Gln Leu Ala Gln Ala Thr Glu
            20                  25                  30

Phe Ser Ala Leu Leu Ser Ser Asp Ile Thr Ala Ser Val Asn Cys Ala
        35                  40                  45

Glu Phe Ile Ala Val His Val Val Pro Asp Gln Leu Met Thr Phe Ser
50                  55                  60

Gly Thr Ser Asp Pro Cys Ala Leu Cys Ser Leu His Ser Ile Gly Lys
65                  70                  75                  80

Ile Gly Gly Ala Gln Asn Arg Asn Tyr Ser Lys Leu Leu Cys Gly Leu
                85                  90                  95

Leu Ser Asp Arg Leu His Ile Ser Pro Asp Arg Val Tyr Ile Asn Tyr
            100                 105                 110

Tyr Asp Met Asn Ala Ala Asn Val Gly Trp Asn Gly Ser Thr Phe Ala
            115                 120                 125
```

<210> SEQ ID NO 38
<211> LENGTH: 209
<212> TYPE: PRT
<213> ORGANISM: Artificial
<220> FEATURE:
<223> OTHER INFORMATION: DNA vaccine DV6

<400> SEQUENCE: 38

```
Met Ser Thr Glu Ser Met Ile Arg Asp Val Glu Leu Ala Glu Glu Ala
1               5                   10                  15

Leu Pro Gln Lys Met Gly Gly Phe Gln Asn Ser Arg Arg Cys Leu Cys
            20                  25                  30

Leu Ser Leu Phe Ser Phe Leu Leu Val Ala Gly Ala Thr Thr Leu Phe
        35                  40                  45

Cys Leu Leu Asn Phe Gly Val Ile Gly Pro Gln Arg Asp Glu Lys Phe
50                  55                  60

Pro Asn Gly Leu Pro Leu Ile Ser Ser Met Ala Gln Thr Leu Thr Leu
65                  70                  75                  80

Arg Met Pro Met Phe Ile Val Asn Thr Asn Val Pro Arg Ala Ser Val
                85                  90                  95

Pro Glu Gly Phe Leu Ser Glu Leu Thr Gln Gln Leu Ala Gln Ala Thr
            100                 105                 110

Glu Phe Ser Ala Leu Leu Ser Ser Asp Ile Thr Ala Ser Val Asn Cys
        115                 120                 125

Ala Glu Phe Ile Ala Val His Val Val Pro Asp Gln Leu Met Thr Phe
130                 135                 140

Ser Gly Thr Ser Asp Pro Cys Ala Leu Cys Ser Leu His Ser Ile Gly
145                 150                 155                 160

Lys Ile Gly Gly Ala Gln Asn Arg Asn Tyr Ser Lys Leu Leu Cys Gly
                165                 170                 175

Leu Leu Ser Asp Arg Leu His Ile Ser Pro Asp Arg Val Tyr Ile Asn
            180                 185                 190

Tyr Tyr Asp Met Asn Ala Ala Asn Val Gly Trp Asn Gly Ser Thr Phe
            195                 200                 205

Ala
```

<210> SEQ ID NO 39
<211> LENGTH: 152
<212> TYPE: PRT
<213> ORGANISM: Artificial

```
<220> FEATURE:
<223> OTHER INFORMATION: DNA vaccine DV7

<400> SEQUENCE: 39

Met Arg Arg Met Leu Leu His Leu Ser Val Leu Thr Leu Ser Cys Val
1               5                   10                  15

Trp Ala Thr Ala Met Glu Met Pro Met Phe Ile Val Asn Thr Asn Val
                20                  25                  30

Pro Arg Ala Ser Val Pro Glu Gly Phe Leu Ser Glu Leu Thr Gln Gln
            35                  40                  45

Leu Ala Gln Ala Thr Glu Phe Ser Ala Leu Leu Ser Ser Asp Ile Thr
        50                  55                  60

Ala Ser Val Asn Cys Ala Glu Phe Ile Ala Val His Val Val Pro Asp
65                  70                  75                  80

Gln Leu Met Thr Phe Ser Gly Thr Ser Asp Pro Cys Ala Leu Cys Ser
                85                  90                  95

Leu His Ser Ile Gly Lys Ile Gly Gly Ala Gln Asn Arg Asn Tyr Ser
            100                 105                 110

Lys Leu Leu Cys Gly Leu Leu Ser Asp Arg Leu His Ile Ser Pro Asp
        115                 120                 125

Arg Val Tyr Ile Asn Tyr Tyr Asp Met Asn Ala Ala Asn Val Gly Trp
    130                 135                 140

Asn Gly Ser Thr Phe Ala Ala Ala
145                 150

<210> SEQ ID NO 40
<211> LENGTH: 124
<212> TYPE: PRT
<213> ORGANISM: Artificial
<220> FEATURE:
<223> OTHER INFORMATION: DNA vaccine DV8

<400> SEQUENCE: 40

Met Pro Met Phe Ile Val Asn Thr Asn Val Pro Arg Ala Ser Val Pro
1               5                   10                  15

Glu Gly Phe Leu Ser Glu Leu Thr Gln Gln Leu Ala Gln Ala Thr Glu
                20                  25                  30

Phe Gln Ala Val His Ala Ala His Ala Glu Ile Asn Glu Phe Ile Ala
            35                  40                  45

Val His Val Val Pro Asp Gln Leu Met Thr Phe Ser Gly Thr Ser Asp
        50                  55                  60

Pro Cys Ala Leu Cys Ser Leu His Ser Ile Gly Lys Ile Gly Gly Ala
65                  70                  75                  80

Gln Asn Arg Asn Tyr Ser Lys Leu Leu Cys Gly Leu Leu Ser Asp Arg
                85                  90                  95

Leu His Ile Ser Pro Asp Arg Val Tyr Ile Asn Tyr Tyr Asp Met Asn
            100                 105                 110

Ala Ala Asn Val Gly Trp Asn Gly Ser Thr Phe Ala
        115                 120

<210> SEQ ID NO 41
<211> LENGTH: 205
<212> TYPE: PRT
<213> ORGANISM: Artificial
<220> FEATURE:
<223> OTHER INFORMATION: DNA vaccine DV9

<400> SEQUENCE: 41

Met Ser Thr Glu Ser Met Ile Arg Asp Val Glu Leu Ala Glu Glu Ala
```

-continued

```
                1               5              10              15
Leu Pro Gln Lys Met Gly Gly Phe Gln Asn Ser Arg Arg Cys Leu Cys
                20                      25                      30

Leu Ser Leu Phe Ser Phe Leu Leu Val Ala Gly Ala Thr Thr Leu Phe
                35                      40                      45

Cys Leu Leu Asn Phe Gly Val Ile Gly Pro Gln Arg Asp Glu Lys Phe
 50                      55                      60

Pro Asn Gly Leu Pro Leu Ile Ser Ser Met Ala Gln Thr Leu Thr Leu
 65                      70                      75                      80

Arg Met Pro Met Phe Ile Val Asn Thr Asn Val Pro Arg Ala Ser Val
                85                      90                      95

Pro Glu Gly Phe Leu Ser Glu Leu Thr Gln Gln Leu Ala Gln Ala Thr
                100                     105                     110

Glu Phe Gln Ala Val His Ala Ala His Ala Glu Ile Asn Glu Phe Ile
                115                     120                     125

Ala Val His Val Pro Asp Gln Leu Met Thr Phe Ser Gly Thr Ser
                130                     135                     140

Asp Pro Cys Ala Leu Cys Ser Leu His Ser Ile Gly Lys Ile Gly Gly
145                     150                     155                     160

Ala Gln Asn Arg Asn Tyr Ser Lys Leu Leu Cys Gly Leu Leu Ser Asp
                165                     170                     175

Arg Leu His Ile Ser Pro Asp Arg Val Tyr Ile Asn Tyr Tyr Asp Met
                180                     185                     190

Asn Ala Ala Asn Val Gly Trp Asn Gly Ser Thr Phe Ala
                195                     200                     205

<210> SEQ ID NO 42
<211> LENGTH: 146
<212> TYPE: PRT
<213> ORGANISM: Artificial
<220> FEATURE:
<223> OTHER INFORMATION: DNA vaccine DV10

<400> SEQUENCE: 42

Met Arg Arg Met Leu Leu His Leu Ser Val Leu Thr Leu Ser Cys Val
 1               5                      10                      15

Trp Ala Thr Ala Met Glu Met Pro Met Phe Ile Val Asn Thr Asn Val
                20                      25                      30

Pro Arg Ala Ser Val Pro Glu Gly Phe Leu Ser Glu Leu Thr Gln Gln
                35                      40                      45

Leu Ala Gln Ala Thr Glu Phe Gln Ala Val His Ala Ala His Ala Glu
 50                      55                      60

Ile Asn Glu Phe Ile Ala Val His Val Pro Asp Gln Leu Met Thr
 65                      70                      75                      80

Phe Ser Gly Thr Ser Asp Pro Cys Ala Leu Cys Ser Leu His Ser Ile
                85                      90                      95

Gly Lys Ile Gly Gly Ala Gln Asn Arg Asn Tyr Ser Lys Leu Leu Cys
                100                     105                     110

Gly Leu Leu Ser Asp Arg Leu His Ile Ser Pro Asp Arg Val Tyr Ile
                115                     120                     125

Asn Tyr Tyr Asp Met Asn Ala Ala Asn Val Gly Trp Asn Gly Ser Thr
                130                     135                     140

Phe Ala
145
```

DNA VACCINE

BACKGROUND OF THE INVENTION

1. Field of the Invention

The present invention relates to a DNA vaccine consisting of a vector expressing a part or the whole of a polypeptide regulating production of an inflammatory cytokine, a pharmaceutical composition comprising the DNA vaccine, and a method of preventing or treating inflammatory diseases by using the pharmaceutical composition.

2. Related. Art

Cytokines are biologically active substances produced by various cells including immune cells. It is also known that one cytokine shows various bioactivities and participates in biological defense such as antiviral action and antitumor action by enhancing immune cells such as lymphocytes, macrophages, NK cells and neutrophils. Cytokines have a feature of acting on one another to contribute to maintenance of homeostasis for biological defense. However, it is noted that cytokines have an action of inducing inflammations and participate in formation of pathologic conditions of various diseases such as rheumatoid arthritis, autoimmune diseases, allergic diseases, fulminant hepatitis, malignant tumors, diabetes and arteriosclerosis. As these diseases become more advanced, cytokines, particularly called inflammatory cytokines such as interleukin-1 (IL-1), interleukin-2 (IL-2), interleukin-6 (IL-6), tumor necrosis factor-α (TNF-α) and interferon-γ (IFN-γ) become induced and detected in blood and tissue (Jiro Imanishi, "Igaku No Ayumi" (Development of Medicine), 181, 750 (1997)).

On one hand, macrophage migration inhibitory factor (abbreviated hereinafter as "MIF") found in 1966 (Bloom B R, et al.: Science 153, 80 (1966)) as a factor to inhibit migration of macrophages in a culture supernatant of lymphocytes from a guinea pig activated by antigen sensitization has been studied for a long time because thereafter its various functions such as isomerase activity, oxidoreductase activity etc. were rediscovered and MIF was found widely in living things ranging from nematodes to vertebrates. At present, MIF is known to be a special peptidic biological active substance which is involved in both natural immunity and acquired immunity for production of cytokines participating in biological defense and which has a plurality of enzyme activities in the same molecule (Rosengren, E., et al.: Mol. Med. 2, 143-149 (1996), Kleemann, R., et al.: J. Mol. Biol. 280, 85-102 (1998)). However, there is no report showing the relationship between these enzyme activities and immunity.

Usually, cytokines are expressed by transcription from genes in the intranuclear genome upon induction with stimulation and produced as proteins one by one by immunocytes. On the other hand, MIF is characterized in that it is previously stored like hormone in cells, and upon external stimulation with an endotoxin or the like, is secreted from a plurality of local tissues including an anterior pituitary gland. Macrophages or T cells stimulated with MIF are not suppressed by glucocorticoids, so MIF is reported to be a biologically active substance counteracting the immunoreaction suppressed by glucocorticoids (Calandra, T,. et al.: Nature 377, 68-71 (1995)).

It is reported that MIF receptors occur on cell surfaces; but this is not necessarily evident. In this relation, it is known that MIF is incorporated for example by endocytosis into cells and binds to Jab1 that is a protein in the cytoplasm (Kleemann, R., et al.: Nature 408, 211-216 (2000)).

Recently, DNA vaccine is developed by the advancement of genetic engineering technology. The DNA vaccine is generally a vaccine using a recombinant plasmid, and a recombinant plasmid comprising a DNA encoding a target antigen is administered to the living body, whereby an amino acid sequence with antigenicity, encoded by the DNA, is expressed in the living body, and an immunoreaction is induced by this amino acid sequence. However, even if a certain specific plasmid DNA is administered to the living body, the degree of immunoreaction induced is not constant, and the degree of immunoreaction varies depending on the type of test animal, the type of DNA and an inoculation method, and it is generally difficult to predict whether the DNA plasmid is useful as DNA vaccine. Under these circumstances, it is attempted to use, for example, interleukin-5 (IL-5) as DNA vaccine for asthma etc. (Hertz, M., et al.: J. Immnol. 167, 3792-3799 (2001)).

SUMMARY OF THE INVENTION

In order that those skilled in the art engaged in drug development to target a receptor on a cell surface develop a drug for suppressing MIF for example, there is usually only a method of developing not a receptor antagonist but an antibody acting directly on MIF or a method of searching a substance binding to an intracellular receptor. Actually, a polyclonal antibody and a monoclonal antibody have been developed and reported to be effective against sepsis or fulminant hepatitis induced by an endotoxin (Bernhagen J, Calandra T, Mitchell R A, et al. MIF is a pituitary-derived cytokine that potentiates lethal endotoxaemia. Nature 1993; 365: 756-9. Kobayashi S, Nishihira J, Watanabe S, et al. Prevention of lethal acute hepatic failure by antimacrophage migration inhibitory factor antibody in mice treated with bacille Calmette-Guerin and lipopolysaccharide. Hepatology 1999; 29: 1752-9). A rheumatic model experiment of Bernhagen et al. is known as a study in which an antigen was administered to a model animal (Bernhagen, J., et. al.: Regulation of the immune response by macrophage migration inhibitory factor: biological and structural features. J. Mol. Med. 76, 151-161 (1998)).

Generally, there are neutralizing antibodies against inflammatory cytokines, among which cytokines released by Th1 cells is particularly inflammatory, and such cytokines include interferon-γ (IFNγ), IL-2 and lymphotoxin (LT). The activity of Th1 in autoimmune diseases and in the inflammatory promoting action of IFN gamma is involved in a large number of autoimmune diseases and inflammatory diseases such as rheumatoid arthritis (RA), multiple sclerosis (MS) and Crohn disease against which neutralizing antibodies against inflammatory cytokines such as IL-1, IL-2, IL-4, IL-5, IL-6, IL-10 and IL-13 are effective. A combination of IL-1 and IL-6 is known to be related to bone destruction in myeloma, against which cytokine neutralizing antibodies (Kawano et al, Nature 332, 83, 1988) and cytokine receptor antibodies (anti-IL-6 antibody etc.) are known to be effective. Recently, various monoclonal antibodies have been produced and used in treatment of, for example, rheumatoid arthritis. Actually, an anti-cytokine therapy using a biological preparation targeting at TNF-α, carried out for a patient with rheumatoid arthritis, has already been practically used. The cytokines are recognized by specific receptors to show their action, so unless the cytokines are recognized by receptors on target cells, no inflammatory reaction is generated. From this viewpoint, soluble receptors for inflammatory cytokines such as TNF-α, IFN-γ, IL-1, IL-2 and IL-6 are used. That is, the presence of the soluble receptors prevents the cytokines from binding to their inherent receptors. However, this method cannot be applied to MIF because its receptor is not found on a cell surface. In addition, mass production of an anti-MIF antibody is difficult because of the toxicity of MIF itself, so it is considered that the development of a pharmaceutical preparation of the anti-MIF antibody is difficult for the time being.

Nonspecific inflammatory bowel diseases (hereinafter abbreviated as IBD) such as ulcerative colitis and Crohn disease are intractable diseases of uncertain cause. Ulcerative colitis is an ulcer-forming inflammatory disease of mainly the large intestine, and Crohn disease is a granulomatous lesion and can occur in any sites in the intestine. The therapy of IBD is mainly drug therapy with a steroid agent or salazopyrine. Particularly, the effectiveness of the steroid agent has been established, but the dose, administration method, adverse effect and accessibility of the drug remain problematic and have been examined. For example, in intractable cases or severe cases of ulcerative colitis, systemic conditions are worse with anemia/hypoproteinemia, and adverse effects such as diarrhea are also caused by administering the drug over a prolonged period. Accordingly, the improvement of systemic conditions by terminating the progress of inflammation, and subsequent operation, are considered to contribute to reduction of death rate, and from this viewpoint, intraarterial infusional therapy with steroid has been attempted by Baba et al. In the intraarterial infusional therapy with steroid, however, nullification examples are about 30% that is a considerable rate, and a reduction in efficacy ratio upon re-administration is also recognized, and inflammatory bowel diseases other than ulcerative colitis have not been examined, and thus Yagita et al. formulated intraarterial infusional therapy of combined use of steroid and ulinastatin and reported good results in IBD as the object (Akikuni Yagita, et al.: the Journal of the Japanese Practical Surgeon Society, 49: p. 590-596 (1988)). Further, such drugs having an inhibitory action on cytokine production are reported to be effective against formation of pathologic conditions of inflammatory bowel diseases, particularly in treatment of inflammatory bowel diseases showing high levels during the active stages of cytokines, particularly TNF-α, IL-6 and IL-8 (Akikuni Yagita: Gastroenterological Surgery, 16: p. 1931-1943 (1993)). However, arterial injection is an administration method with risk and thus there is demand for a therapeutic strategy with less invasion.

Administration of an anti-inflammatory agent such as NSAID or steroid is effective against rheumatoid arthritis. A neutralizing antibody against inflammatory cytokine is effective in radical treatment. Actually, an anti-cytokine therapy using a biological preparation targeting at TNF-α in a patient with rheumatoid arthritis has already been practically used. However, problems such as adverse effect and production of an antibody against the therapeutic antibody are inevitable, and there is a disadvantage that only severely ill patients are therapeutic objectives, and thus there is demand for development of a therapeutic strategy directed to patients having light symptoms.

Assuming that MIF is a gate keeper fulfilling a role in a first stage of biological defense reaction, the inventors intensively advanced analysis study of patients with inflammatory diseases including autoimmune diseases, and as a result they found a phenomenon that against MIF occurring in blood of patients with rheumatoid arthritis and patients with ulcerative colitis, the amount of antibodies having an ability to neutralize its activity is significantly low. Accordingly, the inventors developed a DNA vaccine and formulated treatment strategy of producing antibodies in the patients themselves, and could confirmed effectiveness in an animal experiment. The present invention was completed on the basis of such finding.

The present invention provides a vaccine for a part or the whole of a polypeptide of an enzyme or peptidic hormone regulating production of inflammatory cytokines indicated to participate in forming pathologic conditions of various potential inflammatory diseases or diseases accompanied by inflammations, as well as a pharmaceutical composition comprising the same, and further provides a method of preventing or treating inflammatory diseases and autoimmune diseases including rheumatoid arthritis and Crohn disease.

That is, the present invention provides:

(1) a DNA vaccine comprising a vector comprising at least one gene unit encoding a part or the whole of a polypeptide inducing or producing an inflammatory cytokine;

(2) the DNA vaccine according to the above-mentioned (1), wherein the polypeptide is at least one member of a macrophage migration inhibitory factor, tumor necrosis factor-α, interferon-γ, interleukin-1, interleukin-2 or interleukin-6;

(3) the DNA vaccine according to the above-mentioned (2), wherein the polypeptide is derived from a macrophage migration inhibitory factor;

(4) the DNA vaccine according to the above-mentioned (2), wherein the polypeptide is an enzyme;

(5) the DNA vaccine according to the above-mentioned (1), wherein the vector comprises a gene unit comprising a polynucleotide sequence encoding a polypeptide derived from a macrophage migration inhibitory factor;

(6) the DNA vaccine according to the above-mentioned (5), wherein a part of the polynucleotide sequence in the gene unit comprises a gene unit substituted with a polynucleotide sequence encoding a Th epitope;

(7) the DNA vaccine according to the above-mentioned (5), wherein the vector comprises a gene unit having a polynucleotide sequence encoding an amino acid sequence comprising an amino acid sequence of SEQ ID NO: 1, 2 or 3 substituted partially with an amino acid sequence of SEQ ID NO: 4;

(8) the DNA vaccine according to the above-mentioned (5), wherein the vector comprises a gene unit having a polynucleotide sequence encoding an amino acid sequence comprising an amino acid sequence of SEQ ID NO: 1, 2 or 3 substituted partially with an amino acid sequence of SEQ ID NO: 4 and a gene unit having a polynucleotide sequence of SEQ ID NO: 13;

(9) the DNA vaccine according to the above-mentioned (5), wherein the vector comprises a gene unit encoding an amino acid sequence comprising an amino acid sequence of SEQ ID NO: 1, 2 or 3 substituted partially with an amino acid sequence of SEQ ID NO: 4 and a gene unit having a polynucleotide sequence of SEQ ID NO: 18;

(10) the DNA vaccine according to the above-mentioned (5), wherein the vector comprises a gene unit having a polynucleotide sequence encoding an amino acid sequence comprising an amino acid sequence of SEQ ID NO: 1, 2 or 3 substituted partially with an amino acid sequence of SEQ ID NO: 24 and a gene unit having a polynucleotide sequence of SEQ ID NO: 13 or 18;

(11) the DNA vaccine according to the above-mentioned (1), wherein the vector is a plasmid DNA;

(12) a pharmaceutical composition comprising the DNA vaccine according to any of the above-mentioned (1) to (11);

(13) a pharmaceutical composition according to the above-mentioned (12), which is used in treatment or prevention of an inflammatory disease;

(14) the pharmaceutical composition according to the above-mentioned (13), wherein the inflammatory disease is a disease which has a manifestation of onset of an autoimmune disorder or can be genetically or biochemically determined to potentially have a cause and/or cofactor of the disease, the autoimmune disorder being selected from the group consisting of systemic lupus erythematosus, Sjogren syndrome, rheumatoid arthritis, juvenile-onset diabetes, Wegener granulomatosis, inflammatory bowel disease, polymyositis, dermatomyositis, multiple endocrine failure, Schmidt syndrome, autoimmune uveitis, Addison's disease, adrenalitis, primary biliary cirrhosis, Graves disease, thyroiditis, Hashimoto thyroiditis, autoimmune thyroid disease, pernicious anemia, lupoid hepatitis, demyelinating disease, multiple sclerosis, subacute cutaneous lupus erythematosus, hypoparathyroidism, Dressler syndrome, myasthenia gravis, autoimmune thrombocytopenia, idiopathic thrombocytopenic purpura, hemolytic anemia, autoimmune hemolytic anemia, pemphigus vulgaris, pemphigus, bullous pemphigoid, dermatitis herpetiformis, alopecia areata, autoimmune cystitis, pemphigoid, scleroderma, progressive systemic sclerosis, CREST syndrome (calcicosis, Raynaud esophagus movement disorder, sclerodactyly and teleangiectasia), adult-onset diabetes (type II diabetes), male or female autoimmune infertility, ankylosing spondylitis, ulcerative colitis, Crohn disease, mixed connective-tissue disease, polyarteritis nodosa, systemic sphacelism angiitis, juvenile-onset rheumatoid arthritis, glomerulonephritis, atopic dermatitis, atopic rhinitis, Goodpasture syndrome, Chagas disease, sarcoidosis, rheumatic fever, asthma, recurrent abortion, antiphospholipid syndrome, farmer's lung, erythema multiforme, postcardiotomy syndrome, Cushing syndrome, autoimmune chronic active hepatitis, bird-fancier's lung, allergic encephalomyelitis, toxic skin necrosis lysis, alopecia, Alport syndrome, alveolitis, allergic alveolitis, fibrosing alveolitis, interstitial lung disease, erythema nodosum, pyoderma gangrenosum, blood transfusion reaction, chronic fatigue syndrome, fibromyalgia, Takayasu arteritis, Kawasaki disease, polymyalgia rheumatica, temporal arteritis, giant cell arteritis, Sumter syndrome (triad (also called nasal polyp, eosinophilia, and asthma)), Behcet disease, Caplan syndrome, dengue fever, encephalomyocarditis, endocarditis, myositis, endocardial fibrosis, endophthalmitis, erythema elevatum diutinum, psoriasis, erythroblastosis fetalis, fasciitis accompanied by eosinophilia, Schulman syndrome, Felty syndrome, filariasis, cyclitis, chronic cyclitis, heterochromic cyclitis, Fuchs cyclitis, IgA nephropathy, Henoch-Schonlein Purpura, glomerulonephritis, cardiomyopathy, post-vaccination syndrome, Hodgkin lymphoma and non-Hodgkin lymphoma, renal cell carcinoma, Eaton-Lambert syndrome and relapsing polychondritis;

(15) the pharmaceutical composition according to the above-mentioned (13), wherein the inflammatory disease is accompanied by expression of TNFα, IFN-γ, IL-1, IL-2 or IL-6;

(16) the pharmaceutical composition according to the above-mentioned (13), wherein the disease is rheumatoid arthritis or ulcerative colitis;

(17) the pharmaceutical composition according to the above-mentioned (13), wherein the composition for treatment is an injection;

(18) a method of preventing or treating an inflammatory disease, which comprises administering an effective amount of the DNA vaccine of the above-mentioned (11) or the pharmaceutical composition of the above-mentioned (12) thereby achieving an effective antibody titer; and the like.

By administering the DNA vaccine of the present invention, the antibody titer of an antibody against a polypeptide at which the vaccine targets can be increased, and thus the DNA vaccine of the present invention, a pharmaceutical composition comprising the same, and a method of using the same are useful for prevention or treatment of rheumatoid arthritis, ulcerative colitis etc.

BRIEF DESCRIPTION OF THE DRAWINGS

FIG. 1 is a view showing procedures of preparing the DNA vaccine.

DETAILED DESCRIPTION OF THE INVENTION

Figure 2:
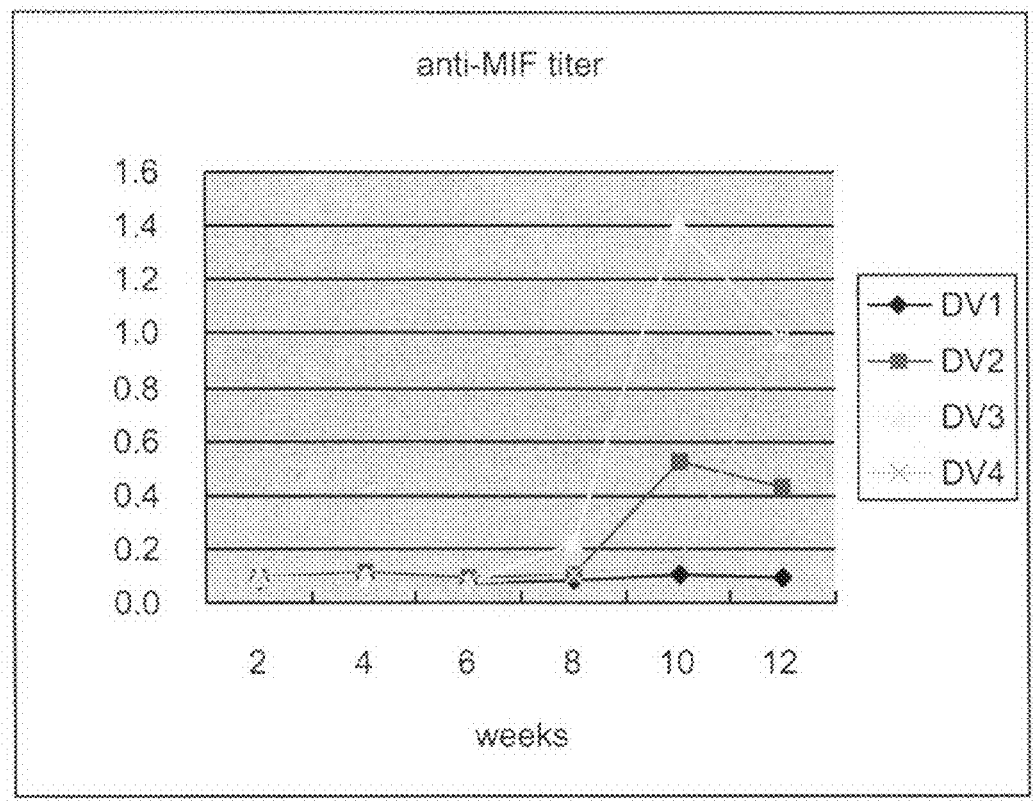
FIG. 2 is a view showing a change in the antibody titer of an anti-MIF antibody in an experiment conducted in Example 10.

Hereinafter, the present invention is described in detail.
1. DNA Vaccine

A first aspect of the invention provides a DNA vaccine comprising a vector comprising at least one gene unit encoding a part or the whole of a polypeptide inducing or producing an inflammatory cytokine. When the DNA vaccine of the present invention is administered to mammals including humans, the polypeptide encoded by the gene unit in the DNA vaccine of the present invention is synthesized in the living body, and this polypeptide acts as an antigen to give rise to immunity. Accordingly, immunization with the DNA vaccine of the present invention is effective in prevention and treatment of diseases associated with the polypeptide inducing or producing an inflammatory cytokine. In this specification, the "vaccine" means a substance capable of generating an immune response. Accordingly, the "DNA vaccine" refers to a DNA acting as a substance capable of generating an immune response among vaccines, that is, a DNA acting as vaccine. As used herein, the "gene unit" refers to the portion of a gene sequence that is necessary for constituting the DNA vaccine, and examples of the gene unit include a polynucleotide encoding a polypeptide serving as an antigen or the site at which the polypeptide is recognized as an antigen, a polynucleotide encoding a signal peptide promoting secretion of the polypeptide, a polynucleotide encoding a Th epitope having an enhancing action on immunoreactivity, a peptide having a length of about 15 to about 50 amino acid residues (U.S. Pat. No. 5,759,551). The DNA vaccine of the present invention can have, in the vector DNA, one or more gene units for enhancing the activity of a target of the vaccine or the activity of the vaccine.

The inflammatory cytokines at which the DNA vaccine of the present invention targets include MIF, tumor necrosis factor-α (TNFα), interferon-γ (ILγ), interleukin-1 (IL-1), interleukin-2 (IL-2) and interleukin-6 (IL-6), and the polypeptide inducing or producing these inflammatory cytokines include MIF, tumor necrosis factor-α (TNFα), interferon-γ (ILγ), interleukin-1 (IL-1), interleukin-2 (IL-2) and interleukin-6 (IL-6). In the present invention, MIF is preferably selected as the inflammatory cytokine-inducible polypeptide. An enzyme inducing or producing the inflammatory cytokine can include, for example, (there are no illustrative substances), a genetic polymorphism of MIF involved in symptoms of psoriasis (Donn R P et al., J. Invest. Dermatol. September 2004; 123(3): 484-7).

The amino acid sequences of MIFs are known in humans (BC013976; SEQ ID NO: 1), in mice (BC024895; SEQ ID NO: 3) and in rats (NM_031051; SEQ ID NO: 2). Among these amino acid sequences, human MIF is particularly preferably used in the present invention.

As used herein, the "MIF-derived peptide" is a peptide having 80% or more (preferably 90% or more, more preferably 95% or more, still more preferably 97% or more) identity with human MIF (SEQ ID NO: 1) and includes peptides comprising (1) an amino acid sequence from which one or more amino acids (preferably about 1 to 30 amino acids, more preferably 1 to 10 amino acids, still more preferably several (for example 1 to 6) amino acids) were deleted, (2) an amino acid sequence to which one or more amino acids (preferably about 1 to 30 amino acids, more preferably 1 to 10 amino acids, still more preferably several (for example 1 to 6) amino acids) were added, (3) an amino acid sequence wherein one or more amino acids (preferably about 1 to 30 amino acids, more preferably 1 to 10 amino acids, still more preferably several (for example 1 to 6) amino acids) were replaced by other amino acids, or (4) an amino acid sequence consisting of a combination of the above amino acid sequences.

The polypeptide of the present invention may be a protein derived from cells of humans or other warm-blooded animals (for example, guinea pig, rat, mouse, chicken, rabbit, pig, sheep, bovine, monkey, etc.) or from any tissues in which such cells are present, or may be a synthetic protein synthesized by genetic engineering or with a commercially available peptide synthesizer.

A part or the whole of the gene encoding the above polypeptide is used as the DNA vaccine. As used herein, the term "a part of the gene" refers to that region of the gene which upon administration as the vaccine, is necessary for producing an antibody against the polypeptide, and the region of the target gene that encodes a peptide region consisting of several (about 1 to 10) amino acids or the whole of the peptide region is used as "a part of the gene".

Specifically, the DNA vaccine is constructed as follows.

The DNA used in the present invention holds a nucleotide sequence such that the target protein (for example human MIF) encoded by the nucleotide sequence can be expressed in the living body. The DNA used in the present invention is a DNA consisting of an expression vector linked with a nucleotide sequence encoding the target protein (for example human MIF). The expression vector is preferably a plasmid vector. The vector useful in preparation of the expression plasmid includes, but is not limited to, vectors containing a constitutive promoter, an inducible promoter, a tissue-specific promoter, or various promoters.

Specific examples of the constitutive promoter include, for example, potent promoters derived from viruses, such as promoters derived from cytomegalovirus (CMV), Rous sarcoma virus (RSV), simian virus-40 (SV40), and herpes simplex virus (HSV). Specific examples of the tissue-specific promoter include muscular β actin promoter. The inducible or regulatory promoter includes, for example, a growth hormone regulatory promoter, a promoter under the control of lac operon sequence, an antibiotic-inducible promoter, and a zinc-inducible metallothionein promoter.

The vector used in the present invention preferably comprises an expression regulatory sequence containing a promoter (for example, the above constitutive or inducible promoter) DNA sequence. The vector may further comprises an enhancer element, an RNA processing sequence such as an intron sequence for transcription or splicing of a polyadenylation signal (derived from, for example, SV40 or bovine growth hormone (BGH)), a signal sequence for secretion of an expression protein, or two or more copies of an immune-stimulating DNA sequence known as CpG motif. The vector may comprise a bacterial sequence of replication origin and/ or a DNA sequence for a selective marker which can be used in antibiotic resistance (for example, kanamycin) or non-antibiotic resistance (for example, β-galactosidase gene).

The DNA used in the present invention may have not only a nucleotide sequence encoding the target protein (for example, human MIF) but also one or more other nucleotide sequences. Specific examples of such other nucleotide sequences include a sequence encoding the Th epitope and a signal peptide for secretion (for example, a signal peptide derived from tumor necrosis factor (TNF) or interleukin-5 (IL-5)). MIF does not have a secretory signal, and thus a gene unit encoding MIF can be used in combination with a gene unit encoding a signal peptide in order to promote secretion of MIF expressed.

The Th epitope, according to a report of Hertz et al. (J. Immunol., 167: 3792-3799 (2001)), produces immunological tolerance by inclusion of its sequence in an antigen, and thus human MIF itself for example can be well used as vaccine. Accordingly, a sequence encoding the Th epitope is preferably substituted for a part (for example, a loop sequence) of the sequence of the target polypeptide. A peptide having such action includes not only the Th epitope but also a partial sequence of hen egg lysozyme (see Nature, 328 (6129): 395-399 (1987)) and a partial sequence of ovalbumin (see J. Immunol. 137 (3): 911-915 (1986)). These peptides, similar to the Th epitope, can also be used in the DNA vaccine of the present invention.

When a plasmid DNA is used as vector, the DNA having a nucleotide sequence encoding the target protein (for example, human MIF) can be prepared in a large amount in a usual manner. For example, a host bacterium is transformed, the resulting transformant is cultured in a large amount, and from the culture, the plasmid DNA can be recovered by techniques known to those skilled in the art, such as an alkaline lysis method. The DNA used in the method of the present invention is preferably a purified plasmid DNA.

2. Pharmaceutical Composition Comprising the DNA Vaccine and a Prophylactic/Therapeutic Method Using the Same The DNA vaccine of the present invention can be provided for example in the form of a pharmaceutical composition prepared by blending with a pharmaceutically acceptable carrier, adjuvant etc. According to the second aspect of the invention, there can be provided a pharmaceutical composition comprising the DNA vaccine described above. According to the third aspect of the invention, there can be provided a method for preventing or treating an inflammatory disease which comprises administering an effective amount of the DNA vaccine or the pharmaceutical composition thereby achieving an effective antibody titer at which the vaccine targets.

The pharmaceutically acceptable carrier used in the present invention is suitable for transfection of DNA vaccine into cells of the living body. Specific examples of such pharmaceutically acceptable carrier include known transfection reagents such as cationic liposome, fluorocarbon emulsion, cochleate, tubule, gold particles, biodegradable microspheres, or cationic polymers. Those skilled in the art can use such transfection reagent to suitably formulate the DNA used in the present invention.

The liposome preferably used in the present invention includes a commercially available liposome and a liposome containing either a cationic lipid or a cationic polymer. The liposome used in a preferable mode of the invention is a liposome containing a mixture of a neutral lipid such as dioleylphosphatidyl ethanolamine (DOPE) or cholesterol and a cationic lipid. A process for producing such liposome is known to those skilled in the art. The cationic polymer unlike the cationic lipid does not have an ester linkage and is thus highly stable in vivo. The structure of the cationic polymer (also called a dendrimer) may be linear or cyclic and may be any of dimer, oligomer and polymer. A cationic polymer in an aqueous solution not having a neutral lipid can also be preferably used in the present invention.

The cochleate that is a stable phospholipid calcium precipitant consisting of phosphatidyl serine, cholesterol, and calcium is also known as a nontoxic and noninflammatory transfection reagent that can be present in a digestive system. The biodegradable microspheres consisting of a polymer such as poly(lactide-co-glycolide) that is polyester can be used in producing microcapsules of the DNA for transfection. The tubule is known as a lipid-based microtube consisting of a lipid of spirally wound two layers packed with their edges joined to each other. When the tubule is used, the DNA can be arranged in the central hollow part thereof for delivery and controlled release into the body of an animal.

The adjuvant for immunization which can be used to prepare the pharmaceutical composition of the present invention is known in the art. Those skilled in the art can suitably select an adjuvant suitable for formation of the pharmaceutical composition. Specific examples of the adjuvant which can be used in the present invention include CpG adjuvant, aluminum hydroxide etc. The pharmaceutical composition of the present invention can be used in an arbitrary dosage form such as capsules, suspension, elixir or solution.

The amount of the vaccine DNA to be combined with a carrier substance for preparing the pharmaceutical composition containing the vaccine DNA given in a single dose depends generally on many factors including the administration route, administration method, the type of nucleotide sequence and expression vector used, the stability and activity (immunogenicity) of the antigen protein or peptide expressed, the condition of a subject, and a disease to be prevented or treated. The amount of the DNA administered depends on the type and amount of the pharmaceutically acceptable carrier (transfection reagent) and adjuvant.

The DNA vaccine of the present invention or a pharmaceutical composition comprising the same can be used for prevention or treatment of an inflammatory disease. The inflammatory disease includes systemic lupus erythematosus, Sjogren syndrome, rheumatoid arthritis, juvenile-onset diabetes, Wegener granulomatosis, inflammatory bowel disease, polymyositis, dermatomyositis, multiple endocrine failure, Schmidt syndrome, autoimmune uveitis, Addison's disease, adrenalitis, primary biliary cirrhosis, Graves disease, thyroiditis, Hashimoto thyroiditis, autoimmune thyroid disease, pernicious anemia, lupoid hepatitis, demyelinating disease, multiple sclerosis, subacute cutaneous lupus erythematosus, hypoparathyroidism, Dressler syndrome, myasthenia gravis, autoimmune thrombocytopenia, idiopathic thrombocytopenic purpura, hemolytic anemia, autoimmune hemolytic anemia, pemphigus vulgaris, pemphigus, bullous pemphigoid, dermatitis herpetiformis, alopecia areata, autoimmune cystitis, pemphigoid, scleroderma, progressive systemic sclerosis, CREST syndrome (calcicosis, Raynaud esophagus movement disorder, sclerodactyly and teleangiectasia), adult-onset diabetes (type II diabetes), male or female autoimmune infertility, ankylosing spondylitis, ulcerative colitis, Crohn disease, mixed connective-tissue disease, polyarteritis nodosa, systemic sphacelism angiitis, juvenile-onset rheumatoid arthritis, glomerulonephritis, atopic dermatitis, atopic rhinitis, Goodpasture syndrome, Chagas disease, sarcoidosis, rheumatic fever, asthma, recurrent abortion, antiphospholipid syndrome, farmer's lung, erythema multiforme, postcardiotomy syndrome, Cushing syndrome, autoimmune chronic active hepatitis, bird-fancier's lung, allergic encephalomyelitis, toxic skin necrosis lysis, alopecia, Alport syndrome, alveolitis, allergic alveolitis, fibrosing alveolitis, interstitial lung disease, erythema nodosum, pyoderma gangrenosum, blood transfusion reaction, chronic fatigue syndrome, fibromyalgia, Takayasu arteritis, Kawasaki disease, polymyalgia rheumatica, temporal arteritis, giant cell arteritis, Sumter syndrome (triad), Behcet disease, Caplan syndrome, dengue fever, encephalomyocarditis, endocarditis, myositis, endocardial fibrosis, endophthalmitis, erythema elevatum diutinum, psoriasis, erythroblastosis fetalis, fasciitis accompanied by eosinophilia, Schulman syndrome, Felty syndrome, filariasis, cyclitis, chronic cyclitis, heterochromic cyclitis, Fuchs cyclitis, IgA nephropathy, Henoch-Schonlein Purpura, glomerulonephritis, cardiomyopathy, post-vaccination syndrome, Hodgkin lymphoma and non-Hodgkin lymphoma, renal cell carcinoma, Eaton-Lambert syndrome and relapsing polychondritis.

The DNA vaccine of the present invention or a pharmaceutical composition comprising the same is useful for prevention or treatment of particularly rheumatoid arthritis, ulcerative colitis etc.

The DNA vaccine or the pharmaceutical composition comprising the same can be administered directly to the muscle or skin. A gene gun can be used to administer the DNA vaccine of the present invention. Subcutaneous injection, intracutaneous injection, percutaneous douche and other injection methods, for example, intraperitoneal, intravenous or inhalation administration, and oral administration are also feasible, and the administration route is not particularly limited. Booster inoculation can also be carried out.

The DNA vaccine or the pharmaceutical composition according to the present invention, when administered to a mammal (patient), is administered in an amount effective for prevention or treatment of the diseases (for example, rheumatoid arthritis, ulcerative colitis etc.) described above and is administered generally in an amount of 1 µg to 2000 µg.

By administrating an effective amount of the DNA vaccine or the pharmaceutical composition to a patient, the antibody titer effective against the polypeptide at which the vaccine targets can be obtained in the patient.

EXAMPLES AND COMPARATIVE EXAMPLES

The present invention is described in more detail by reference to the Comparative Examples and Examples, but the present invention is not limited to these examples.

Comparative Example 1

Construction of Mouse MIF Expression Plasmid Vector

Mouse MIF cDNA was amplified by using total RNA, as a material, prepared from RAW264.7 cells by RT-PCR method with primer B-1U shown by SEQ ID NO: 6 and primer X-348L shown by SEQ ID NO: 9. The reaction system for synthesis of cDNA was composed of 50 mM Tris-HCl (pH 8.3), 50 mM potassium chloride, 10 mM magnesium chloride, 0.5 mM spermidine, 10 mM dithiothreitol, 1 mM dNTP, 40 U RNase inhibitor, 0.2 µM random oligonucleotide (9 residues), 30 U AMV reverse transcriptase and 2 µg of RNA, and the total volume was 25 µl. The reaction was carried out at 42° C. for 60 minutes. The PCR solution was composed of 10 mM Tris-HCl, pH 9.0, 50 mM potassium chloride, 0.1% Triton X-100, 1.5 mM magnesium chloride, 0.2 µM primers B-1U (SEQ ID NO: 6) and X-348L (SEQ ID NO: 9), 1 mM dNTP and 10 U Taq DNA polymerase, and the total volume was 25 µl. In PCR, after (i) a reaction at 94° C. for 5 minutes, (ii) a cycle consisting of a reaction at 94° C. for 10 seconds, at 56° C. for 10 seconds and at 72° C. for 1 minute was repeated 25 times, and finally an extension reaction at 72° C. for 5 minutes was carried out, whereby a mouse MIF cDNA fragment was obtained. The cDNA fragment was purified, then cloned into a restriction enzyme site BamHI/XhoI of plasmid vector pcDNA3.1 to give plasmid vector pcDNA3.1/MIF (referred to as DV1: SEQ ID NO: 32) expressing mouse MIF.

Example 1

Preparation of DNA Vaccine

Figure 1:
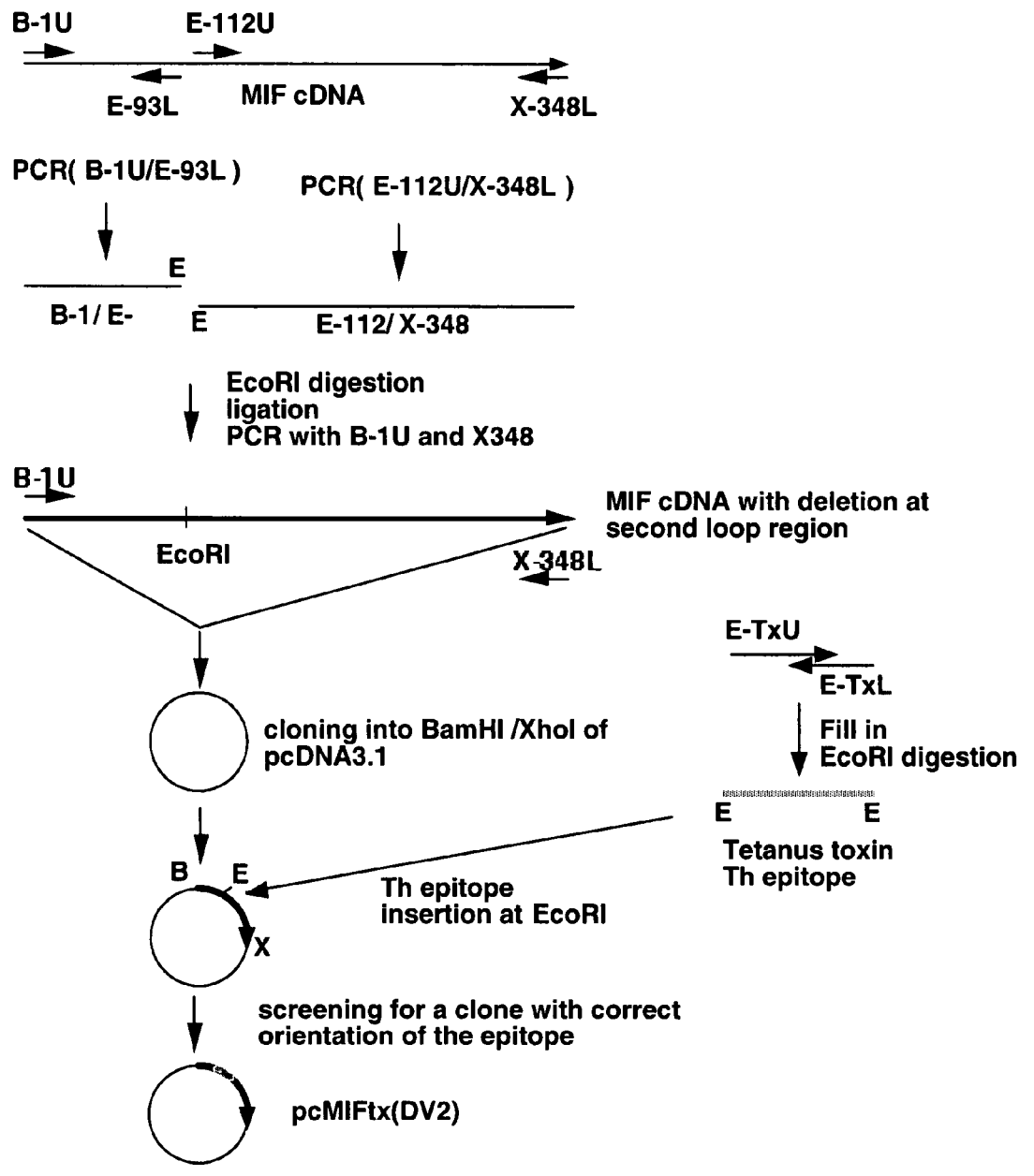

A mutant MIF expression plasmid vector (pcDNA3.1/MIF/Ttx (DV2)) having tetanus toxin Th epitope (SEQ ID NO: 4) was prepared as the DNA vaccine. The procedure is shown in FIG. 1.

Using a pair of primers B-1U (SEQ ID NO: 6) and E-93L (SEQ ID NO: 7) or a pair of primers E-112U (SEQ ID NO: 8) and X-348L (SEQ ID NO: 9), PCR was carried out with MIF cDNA as a template. The reaction solution in this reaction was composed of 1 ng of the above cDNA, 10 mM Tris-HCl, pH 9.0, 50 mM potassium chloride, 0.1% Triton X-100, 1.5 mM magnesium chloride, 0.2 µM of the above primers, 1 mM dNTP and 10 U Taq DNA polymerase, and the final total volume was 25 µl. In PCR, after (i) a reaction at 94° C. for 5 minutes, (ii) a cycle consisting of a reaction at 94° C. for 10 seconds, at 56° C. for 10 seconds and at 72° C. for 1 minute was repeated 25 times, and finally an extension reaction at 72° C. for 5 minutes was carried out. As a result, MIF cDNA fragments, that is, B-1/E-93 and E-112/X-348 were obtained. These fragments were treated with a restriction enzyme EcoRI and ligated with T4 DNA ligase. Using the resulting fragment as a template, PCR was carried out with B-1U and X-348L as primers. The reaction solution in this reaction was composed of 1 ng of the DNA fragment obtained above, 10 mM Tris-HCl, pH 9.0, 50 mM potassium chloride, 0.1% Triton X-100, 1.5 mM magnesium chloride, 0.2 µM of the above primers, 1 mM dNTP, and 10 U Taq DNA polymerase, and the final volume was 25 µl. In PCR, after (i) a reaction at 94° C. for 5 minutes, (ii) a cycle consisting of a reaction at 94° C. for 10 seconds, at 56° C. for 10 seconds and at 72° C. for 1 minute was repeated 25 times, and finally an extension reaction at 72° C. for 5 minutes was carried out. As a result, a mutant MIF cDNA having a deficiency of a second loop and having an EcoRI site substituted therefore was obtained. This cDNA was treated with BamHI and XhoI and inserted into a BamHI/XhoI site of pcDNA 3.1. The mutant MIF expression plasmid vector thus obtained was designated pcDNA 3.1/MIFd2 (referred to as DV0). The polypeptide expressed by this vector is represented by SEQ ID NO: 33 in the Sequence Listing.

Separately, a tetanus toxin Th epitope (SEQ ID NO: 4) was prepared by DNA extension reaction. That is, the extension reaction was carried out at 37° C. for 30 minutes by using E-TxU (SEQ ID NO: 10) and E-TxL (SEQ ID NO: 11) as primer/template and Klenow fragment as enzyme in 25 µl (final volume) of solution containing 10 mM Tris-HCl, pH 9.0, 50 mM potassium chloride, 0.1% Triton X-100, 1.5 mM magnesium chloride, 1 µM of the above primers and 1 mM dNTP. The product (SEQ ID NO: 5) was treated with EcoRI, then inserted into an EcoRI site of the MIF expression vector DV0 prepared above, to give a mutant MIF expression plasmid vector (pcDNA3.1/MIF/Ttx (referred to as DV2)) having the tetanus toxin Th epitope. The peptide obtained by this expression plasmid vector is represented by SEQ ID NO: 34 in the Sequence Listing.

Example 2

Preparation of DNA Vaccine

MIF is a protein having no secretory signal. In expectation of enhancement of the antigenicity of MIF by positive secretion, a secretory signal was fused with the amino terminus thereof. Herein, a secretory signal of tumor necrosis factor (TNF) was used. It is known that TNF is partially expressed as membrane protein, and it is expected that MIF is also partially expressed as membrane protein by a secretory signal of TNF. A DNA (SEQ ID NO: 13) encoding a secretory signal peptide (SEQ ID NO: 12) of TNF was introduced into DV2 that is the mutant MIF expression plasmid vector prepared in Example 1 to prepare pcDNA3.1/TNFsignal/MIF/Ttx (referred to as DV3). The peptide obtained by this expression plasmid vector is represented by SEQ ID NO: 35 in the Sequence Listing.

PCR was carried out with a pair of primers B-TsU (SEQ ID NO: 14) and soe-TsL (SEQ ID NO: 15) by using, as a template, the DNA (SEQ ID NO: 13) encoding a secretory signal peptide of TNF, or with a pair of soe-Ts-MIFU (SEQ ID NO: 16) and X-348L (SEQ ID NO: 8) by using DV2 as a template. The reaction solution in this reaction was composed of 1 ng of the above cDNA, 10 mM Tris-HCl, pH 9.0, 50 mM potassium chloride, 0.1% Triton X-100, 1.5 mM magnesium chloride, 0.2 μM of the above primers, 1 mM dNTP and 10 U Taq DNA polymerase, and the final volume was 25 μl. In PCR, after (i) a reaction at 94° C. for 5 minutes, (ii) a cycle consisting of a reaction at 94° C. for 10 seconds, at 56° C. for 10 seconds and at 72° C. for 1 minute was repeated 25 times, and finally an extension reaction at 72° C. for 5 minutes was carried out. Using the resulting reaction product as a template, PCR was carried out with a pair of primers B-TsU (SEQ ID NO: 14) and X-348L (SEQ ID NO: 8). The reaction solution was composed of 1 ng of the above cDNA, 10 mM Tris-HCl, pH 9.0, 50 mM potassium chloride, 0.1% Triton X-100, 1.5 mM magnesium chloride, 0.2 μM of the above primers, 1 mM dNTP, and 10 U Taq DNA polymerase, and the final volume was 25 μl. In PCR, after (i) a reaction at 94° C. for 5 minutes, (ii) a cycle consisting of a reaction at 94° C. for 10 seconds, at 56° C. for 10 seconds and at 72° C. for 1 minute was repeated 25 times, and finally an extension reaction at 72° C. for 5 minutes was carried out. The resulting fragment was treated with restriction enzymes BamHI/XhoI and inserted into a BamHI/XhoI site of pcDNA 3.1.

Example 3

Preparation of DNA Vaccine pcDNA3.1/IL-5signal/MIF/Ttx (referred to as DV4) was prepared by introducing a DNA (SEQ ID NO: 18) encoding a secretory signal peptide (SEQ ID NO: 17) of IL-5. The DNA encoding a secretory signal peptide of IL-5 was prepared by DNA extension reaction. That is, the extension reaction was carried out at 37° C. for 30 minutes by using 5sU (SEQ ID NO: 19) and 5sL (SEQ ID NO: 20) as primer/template and Klenow fragment as enzyme in 25 μl (final volume) of solution containing 10 mM Tris-HCl, pH 9.0, 50 mM potassium chloride, 0.1% Triton X-100, 1.5 mM magnesium chloride, 1 μM of the above primers and 1 mM dNTP. PCR was carried out with a pair of primers B-5sU (SEQ ID NO: 21) and soe-5sL (SEQ ID NO: 22) by using this reaction product as a template, or with a pair of soe-5s-MIFU (SEQ ID NO: 23) and X-348L (SEQ ID NO: 8) by using DV2 as a template. The reaction solution in this reaction was composed of 1 ng of the above cDNA, 10 mM Tris-HCl, pH 9.0, 50 mM potassium chloride, 0.1% Triton X-100, 1.5 mM magnesium chloride, 0.2 µM of the above primers, 1 mM dNTP and 10 U Taq DNA polymerase, and the final volume was 25 µl. In PCR, after (i) a reaction at 94° C. for 5 minutes, (ii) a cycle consisting of a reaction at 94° C. for 10 seconds, at 56° C. for 10 seconds and at 72° C. for 1 minute was repeated 25 times, and finally an extension reaction at 72° C. for 5 minutes was carried out. Using the resulting reaction product as a template, PCR was carried out with a pair of primers B-5sU (SEQ ID NO: 21) and X-348L (SEQ ID NO: 8). The reaction solution was composed of 1 ng of the above cDNA, 10 mM Tris-HCl, pH 9.0, 50 mM potassium chloride, 0.1% Triton X-100, 1.5 mM magnesium chloride, 0.2 µM of the above primers, 1 mM dNTP, and 10 U Taq DNA polymerase, and the final volume was 25 µl. In PCR, after (i) a reaction at 94° C. for 5 minutes, (ii) a cycle consisting of a reaction at 94° C. for 10 seconds, at 56° C. for 10 seconds and at 72° C. for 1 minute was repeated 25 times, and finally an extension reaction at 72° C. for 5 minutes was carried out. The resulting fragment was treated with restriction enzymes BamHI/XhoI and inserted into a BamHI/XhoI site of pcDNA 3.1. A peptide obtained by this expression plasmid vector is represented by SEQ ID NO: 36 in the Sequence Listing.

Example 4

Preparation of DNA Vaccine

A peptide known to have the same effect as that of Th epitope used in Example 1 includes a partial peptide of hen egg lysozyme or ovalbumin. In this example, pcDNA3.1/MIF/HEL (referred to as DV5) wherein the Th epitope of DV2 was replaced by a DNA encoding a peptide having an amino acid sequence (SEQ ID NO: 24) in positions 81 to 95 in hen egg lysozyme was prepared.

A DNA fragment (SEQ ID NO: 25) encoding a peptide having an amino acid sequence (SEQ ID NO: 24) in positions 81 to 95 in hen egg lysozyme was prepared by DNA extension reaction by using the following oligo DNAs: primer E-HLU (SEQ ID NO: 26) and primer E-HLL (SEQ ID NO: 27). That is, the extension reaction was carried out at 37° C. for 30 minutes by using E-HLU (SEQ ID NO: 26) and E-HLL (SEQ ID NO: 27) as primer/template and Klenow fragment as enzyme in 25 µl (final volume) of solution containing 10 mM Tris-HCl, pH 9.0, 50 mM potassium chloride, 0.1% Triton X-100, 1.5 mM magnesium chloride, 1 µM of the above primers and 1 mM dNTP. The product was treated with EcoRI and then inserted for substitution into an EcoRI site of the MIF expression vector (DV2) prepared in Example 2, whereby a mutant MIF expression plasmid vector (pcDNA3.1/MIF/HEL (DV5)) having a peptide having the amino acid sequence in positions 81 to 95 in hen egg lysozyme was obtained. A peptide obtained by this expression plasmid vector is represented by SEQ ID NO: 37 in the Sequence Listing.

Example 5

Preparation of DNA Vaccine

A mutant MIF expression plasmid vector pcDNA3.1/TNFsignal/MIF/HEL (referred to as DV6) wherein the Th epitope of DV3 prepared in Example 2 was replaced by an amino acid sequence (SEQ ID NO: 24) in positions 81 to 95 in hen egg lysozyme was prepared.

The DNA fragment encoding a peptide having an amino acid sequence in positions 81 to 95 in hen egg lysozyme, prepared in Example 4, was inserted for substitution into an EcoRI site of DV3 in the same manner as above, to prepare a mutant MIF expression plasmid vector pcDNA3.1/TNFsignal/MIF/HEL (DV6) having a peptide having the amino acid sequence in positions 81 to 95 in hen egg lysozyme. A peptide obtained by this expression plasmid vector is represented by SEQ ID NO: 38 in the Sequence Listing.

Example 6

Preparation of DNA Vaccine

A mutant MIF expression plasmid vector pcDNA3.1/IL-5signal/MIF/HEL (referred to as DV7) wherein the Th epitope of DV4 was replaced by an amino acid sequence (SEQ ID NO: 24) in positions 81 to 95 in hen egg lysozyme was prepared in the same manner as in Example 4.

The DNA fragment encoding a peptide having an amino acid sequence in positions 81 to 95 in hen egg lysozyme, prepared in Example 4, was inserted for substitution into an EcoRI site of DV4 in the same manner as above, to prepare a mutant MIF expression plasmid vector pcDNA3.1/IL-5signal/MIF/HEL (DV7) having a peptide having the amino acid sequence in positions 81 to 95 in hen egg lysozyme. A peptide obtained by this expression plasmid vector is represented by SEQ ID NO: 39 in the Sequence Listing.

Example 7

Preparation of DNA Vaccine

In this example, pcDNA3.1/MIF/OVA (referred to as DV8) introduced into a mutant MIF expression plasmid vector pcDNA3.1/MIF having a peptide having an amino acid sequence (SEQ ID NO: 28) in positions 325 to 336 in ovalbumin was prepared.

A DNA fragment (SEQ ID NO: 29) encoding a peptide having an amino acid sequence in positions 325 to 336 in ovalbumin was prepared by DNA extension reaction by using the following oligo DNAs: primer E-OVU (SEQ ID NO: 30) and primer E-OVL (SEQ ID NO: 31). That is, the extension reaction was carried out at 37° C. for 30 minutes by using E-OVL (SEQ ID NO: 31) and E-OVL (SEQ ID NO: 31) as primer/template and Klenow fragment as enzyme in 25 µl (final volume) of solution containing 10 mM Tris-HCl, pH 9.0, 50 mM potassium chloride, 0.1% Triton X-100, 1.5 mM magnesium chloride, 1 µM of the above primers and 1 mM dNTP. The product was treated with EcoRI and then inserted for substitution into an EcoRI site of the MIF expression vector (DV2) prepared in Example 2, whereby a mutant MIF expression plasmid vector (pcDNA3.1/MIF/OVA (DV8)) having a peptide having the amino acid sequence in positions 325 to 336 in ovalbumin was obtained. A peptide obtained by this expression plasmid vector is represented by SEQ ID NO: 40 in the Sequence Listing.

Example 8

Preparation of DNA Vaccine

A mutant MIF expression plasmid vector pcDNA3.1/TNFsignal/MIF/OVA (referred to as DV9) wherein the Th epitope of DV3 prepared in Example 2 was replaced by a peptide having an amino acid sequence (SEQ ID NO: 28) in positions 325 to 336 in ovalbumin was prepared.

The DNA fragment encoding a peptide having an amino acid sequence in positions 325 to 336 in ovalbumin, prepared in Example 7, was inserted for substitution into an EcoRI site of DV3 in the same manner as above, to prepare a mutant MIF expression plasmid vector pcDNA3.1/TNFsignal/MIF/OVA (DV9) having a peptide having the amino acid sequence in positions 325 to 336 in ovalbumin. A peptide obtained by this expression plasmid vector is represented by SEQ ID NO: 41 in the Sequence Listing.

Example 9

Preparation of DNA Vaccine

A mutant MIF expression plasmid vector pcDNA3.1/IL-5signal/MIF/OVA (referred to as DV10) wherein the Th epitope of DV4 was replaced by a peptide having an amino acid sequence (SEQ ID NO: 28) in positions 325 to 336 in ovalbumin was prepared in the same manner as in Example 7.

The DNA fragment encoding a peptide having an amino acid sequence in positions 325 to 336 in ovalbumin, prepared in Example 7, was inserted for substitution into an EcoRI site of DV4 in the same manner as above, to prepare a mutant MIF expression plasmid vector pcDNA3.1/IL-5signal/MIF/OVA (DV10) having a peptide having the amino acid sequence in positions 325 to 336 in ovalbumin. A peptide obtained by this expression plasmid vector is represented by SEQ ID NO: 42 in the Sequence Listing.

Example 10

The vaccines (DV1 to DV4) obtained in Examples 1 to 3 were administered respectively to groups each consisting of 6 mice (subcutaneously administered in a dose of 100 µg into 2 different sites 6 times at 2-week intervals), and 2, 4, 6, 8, 10 and 12 weeks thereafter, blood was collected from arbitrary one mouse in each group, and the anti-MIF antibody titer was measured by ELISA. Measurement of the anti-MIF antibody titer was carried out by reacting recombinant MIF immobilized on a 96-well plate with the plasma diluted with phosphate buffered saline containing 1 mM EDTA and quantifying the bound antibody. The results are shown in FIG. 2. As shown in FIG. 2, it was found that effective antibody titers could be obtained when DV2 to DV4 DNA vaccines were used.

Example 11

Induction of Arthritis

Induction of arthritis was carried out according to a method of Kawabata et al. (Arthritis and Rheumatism, 50, 660-668, 2004). That is, a cocktail of monoclonal antibodies (500 µg of D1, D8, A2 and F10, Chondrex, Redmond, Wash.) against type II collagen was dissolved in 500 µl of PBS and administered intraperitoneally to mice to which the DNA vaccine prepared in Example 1 or the control DNA had been administered, and 72 hours thereafter, 50 µg of LPS/100 µl of PBS was intraperitoneally administered to induce arthritis.

Figure 3:
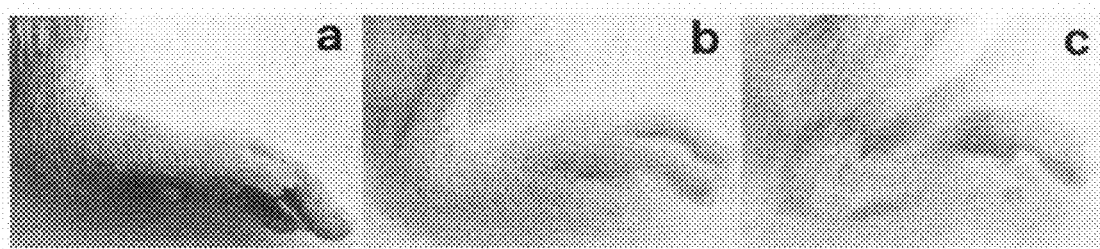
FIG. 3 is a view showing the effect of the DNA vaccine on arthritis in an experiment conducted in Example 11.

As shown in FIG. 3, the results indicated that typical swelling was recognized in a leg joint in the control mouse (antibody negative) (FIG. 2-*a*), while this event was significantly inhibited in the MIF/Th DNA vaccine administration group (antibody positive) (FIG. 2-*b*) and hardly distinguished from that of the untreated mouse of the same age (FIG. 2-*c*).

Example 12

Histological Grading of DNA Vaccine for Arthritis

Figure 4:
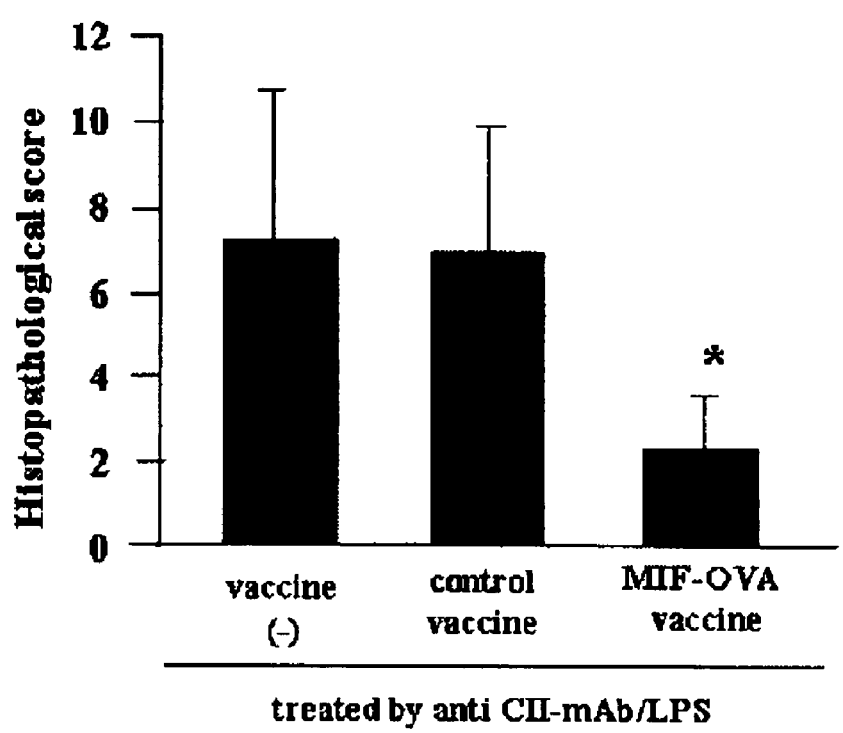
FIG. 4 is a view showing histological grading of the DNA vaccine for arthritis in an experiment conducted in Example 12.

Balb/c mice (9 mice in each group) were subcutaneously administered 6 times with saline, MIF cDNA control (DV1) vaccine, or MIF-OVA (DV8) vaccine, then subjected to operation of developing anti-collagen antibody cocktail arthritis, and sacrificed after 1 week, and with respect to arthritis in joints of both paws and in joints of legs, outgrowths of synovial membrane, cartilage destruction and pannus formation were observed to determine histological grading. The results are shown in FIG. 4. As a result, it was revealed that the degrees of arthritis and joint destruction in the MIF-OVA (DV8) vaccine-administrated mice are significantly lower than those of the control vaccine-administrated mice.

INDUSTRIAL APPLICABILITY

According to the present invention, there can be provided a DNA vaccine effective against rheumatoid arthritis, ulcerative colitis etc. Specifically, the DNA vaccine comprising the MIF gene can be administered as a pharmaceutical composition to increase the antibody titer and prevent or treat the diseases described above.

---

What is claimed is:

1. A DNA vaccine comprising a vector comprising a polynucleotide sequence encoding an amino acid sequence comprising the amino acid sequence of SEQ ID NO: 1, 2 or 3 wherein the amino acid sequence has a second loop sequence substituted with an amino acid sequence selected from the group consisting of SEQ ID NO: 4, 24 or 28.

2. The DNA vaccine according to claim 1, wherein:
the vector comprises a first gene unit comprising said polynucleotide sequence of claim 1, and
the vector further comprises a second gene unit comprising a polynucleotide sequence of SEQ ID NO: 18.

3. The DNA vaccine according to claim 1, wherein:
the vector comprises a first gene unit comprising said polynucleotide sequence of claim 1, and
the vector further comprises a second gene unit comprising a polynucleotide sequence of SEQ ID NO: 13 or 18.

4. The DNA vaccine according to claim 1, wherein the vector is a plasmid DNA.

5. A pharmaceutical composition comprising the DNA vaccine according to claim 1.

* * * * *